(12) United States Patent
Walker

(10) Patent No.: US 9,421,357 B2
(45) Date of Patent: Aug. 23, 2016

(54) SYSTEMS, APPARATUSES, AND METHODS FOR PROVIDING NON-TRANSCRANIAL ELECTROTHERAPY

(71) Applicant: MedRelief Inc., Bethesda, MD (US)

(72) Inventor: Christian Walker, Kensington, MD (US)

(73) Assignee: MEDRELIEF INC., Bethesda, MD (US)

( * ) Notice: Subject to any disclaimer, the term of this patent is extended or adjusted under 35 U.S.C. 154(b) by 0 days.

(21) Appl. No.: 14/602,926

(22) Filed: Jan. 22, 2015

(65) Prior Publication Data

US 2015/0217107 A1 Aug. 6, 2015

Related U.S. Application Data

(62) Division of application No. 13/000,332, filed as application No. PCT/US2009/047952 on Jun. 19, 2009, now Pat. No. 8,972,024.

(60) Provisional application No. 61/074,530, filed on Jun. 20, 2008.

(51) Int. Cl.
*A61N 1/04* (2006.01)
*A61H 39/00* (2006.01)
(Continued)

(52) U.S. Cl.
CPC ............ *A61N 1/0452* (2013.01); *A61H 39/002* (2013.01); *A61N 1/0408* (2013.01); *A61N 1/0464* (2013.01); *A61N 1/0472* (2013.01); *A61N 1/36003* (2013.01); *A61N 1/36021* (2013.01); *A61H 2201/1604* (2013.01); *A61H 2201/165* (2013.01); *A61H 2205/02* (2013.01); *A61H 2205/026* (2013.01);
(Continued)

(58) Field of Classification Search
CPC ................... A61H 39/002; A61H 2201/1604; A61H 2201/165; A61H 2205/02; A61H 2205/026; A61N 1/0408; A61N 1/0464; A61N 1/36003; A61N 1/0472; A61N 1/36021; A61N 1/0452; A61N 1/0468; A61N 1/205; A61N 1/323
See application file for complete search history.

(56) References Cited

U.S. PATENT DOCUMENTS 3,797,500 A * 3/1974 Porter ................ A61N 1/36014
331/111
4,586,509 A 5/1986 Liss et al.
(Continued)

FOREIGN PATENT DOCUMENTS

JP 2001-293097 A 10/2001

OTHER PUBLICATIONS

Baribault et al., "The G-Protein-Coupled Receptor GPR103 Regulates Bone Formation," *Molecular and Cellular Biology* 26(2):709-717, Jan. 2006.
(Continued)

*Primary Examiner* — Catherine Voorhees
(74) *Attorney, Agent, or Firm* — Seed IP Law Group PLLC

(57) ABSTRACT

Systems, apparatuses, and methods for providing non-transcranial electrical stimuli to a biological subject may employ a support structure, at least one waveform generator, and at least a first electrode and a second electrode. The system can be sized and dimensioned to be worn on a head of the biological subject and operable to deliver non-transcranial electrical stimuli to at least one of the temporomandibular joints of the biological subject.

13 Claims, 10 Drawing Sheets

(51) Int. Cl.
*A61N 1/20* (2006.01)
*A61N 1/32* (2006.01)
*A61N 1/36* (2006.01)

(52) U.S. Cl.
CPC .............. *A61N 1/0468* (2013.01); *A61N 1/205* (2013.01); *A61N 1/323* (2013.01)

(56) References Cited

U.S. PATENT DOCUMENTS

| | | | |
|---|---|---|---|
| 4,942,880 A | 7/1990 | Slovak | |
| 5,273,033 A | 12/1993 | Hoffman | |
| 5,514,175 A * | 5/1996 | Kim ................... | A61H 39/002 607/115 |
| 6,011,994 A | 1/2000 | Kronberg | |
| 6,321,119 B1 | 11/2001 | Kronberg | |
| 6,535,767 B1 | 3/2003 | Kronberg | |
| 7,117,034 B2 | 10/2006 | Kronberg | |
| 2003/0018368 A1 | 1/2003 | Ansarinia | |
| 2003/0125661 A1 | 7/2003 | Yerushalmy | |
| 2004/0267333 A1 | 12/2004 | Kronberg | |
| 2005/0165460 A1 * | 7/2005 | Erfan ................... | A61N 1/326 607/57 |
| 2006/0085049 A1 | 4/2006 | Cory et al. | |
| 2006/0094924 A1 | 5/2006 | Riehl | |
| 2006/0293724 A1 | 12/2006 | Kronberg et al. | |
| 2008/0015463 A1 | 1/2008 | Goldstein | |
| 2008/0039901 A1 | 2/2008 | Kronberg et al. | |
| 2008/0215113 A1 | 9/2008 | Pawlowicz | |
| 2009/0131739 A1 | 5/2009 | Shalev | |

OTHER PUBLICATIONS

Bowler et al., "G-Protein Coupled Receptors in Bone," *Frontiers in Bioscience* 3:d769-780, Aug. 1, 1998.

Chang et al., "Pulsed electromagnetic fields prevent osteoporosis in an ovariectomized female rat model: a prostaglandin $E_2$-associated process," *Bioelectromagnetics* 24(3):189-198, Apr. 2003.

Extended European Search Report, dated Nov. 29, 2011, for European Patent Application No. 09767825.4, 7 pages.

Fredericks et al., "Effects of pulsed electromagnetic field stimulation on distraction osteogenesis in the rabbit tibial leg lengthening model," *J. Pediatr. Orthop.* 23(4):478-483, Jul.-Aug. 2003.

International Preliminary Report on Patentability, issued Dec. 21, 2010, for International Patent Application No. PCT/US2009/047952, 6 pages.

International Search Report, mailed Feb. 2, 2010, for International Patent Application No. PCT/US2009/047952, 4 pages.

Tabrah et al., "Bone Density Changes in Osteoporosis-Prone Women Exposed to Pulsed Electromagnetic Fields (PEMFs)," *Journal of Bone and Mineral Research* 5(5):437-442, 1990.

Wright et al., "Biopsychosocial differences between high-risk and low-risk patients with acute TND-related pain," *JADA* 135:474-483, Apr. 2004.

Written Opinion of the International Searching Authority, mailed Feb. 2, 2010, for International Patent Application No. PCT/US2009/047952, 5 pages.

* cited by examiner

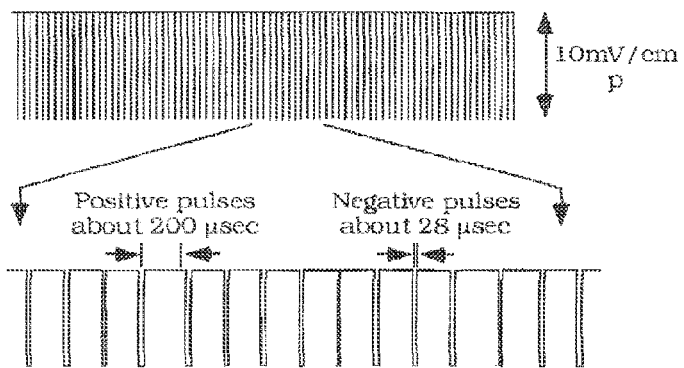
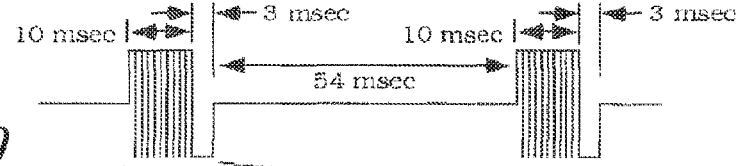
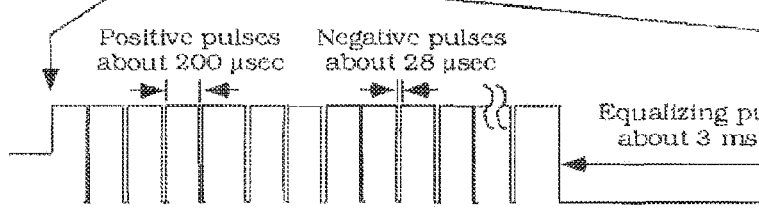
FIG. 8
FIG. 9

SYSTEMS, APPARATUSES, AND METHODS FOR PROVIDING NON-TRANSCRANIAL ELECTROTHERAPY

CROSS-REFERENCES TO RELATED APPLICATIONS

This application is a U.S. national stage application filed under 35 U.S.C. §371 of International Patent Application PCT/US2009/047952, accorded an international filing date of Jun. 19, 2009, which claims the benefit under 35 U.S.C. §119(e) of U.S. Provisional Patent Application No. 61/074,530, filed Jun. 20, 2008; both of which are incorporated herein by reference in their entirety.

BACKGROUND

1. Technical Field

This disclosure generally relates to the field of electrotherapy and, more particularly, to system, devices, and methods for providing non-transcranial electrotherapy to a biological subject.

2. Description of the Related Art

The term temporomandibular joint (TMJ) disorder, sometimes referred to as temporomandibular disorder, TMJ syndrome, or myofacial pain dysfunction syndrome, encompasses a whole spectrum of conditions and diseases associated with pain and/or dysfunction in the jaw joint and the muscles that control jaw movement. These conditions and diseases include injured or damaged tissues affecting the function of the TMJ, discomfort or pain in the muscles that control jaw function, displacement of a TMJ disc, a dislocated jaw, an injury to the condyle, derangements of the articulating elements in the TMJ, degenerative or inflammatory joint disorders, progressive degenerative and very painful breakdown of TMJ cartilage, tenderness and pain of the TMJ, and pivoting of the jaw. It has been estimated that about 8 to 15 percent of women and about 3 to 10 percent of men experience pain associated with TMJ disorder. There are no known cures for TMJ disorder.

Conventional conservative treatments for TMJ disorder include eating soft foods, applying ice packs, avoiding extreme jaw movements, learning techniques for relaxing and reducing stress, as well as short-term use of over-the-counter pain medicines, nonsteroidal anti-inflammatory drugs, muscle relaxants, or anti-depressants. Conventional conservative treatments often provide only temporary pain relief.

Conventional irreversible TMJ disorder treatments include surgery, orthodontics to change the bite, crown and bridge work to balance the bite, grinding down teeth to bring the bite into balance, and repositioning splints (e.g., orthotics), which permanently alter the bite. Surgical treatments, such as the replacement of jaw joints with artificial implants, are often irreversible and in some cases may cause severe pain and permanent jaw damage. For example, some artificial implants may fail to function properly or may break apart in the jaw over time.

Bone and other tissues such as cartilage respond to electrical signals in a physiologically useful manner. For example, electric and electromagnetic fields regulate extra-cellular matrix synthesis and stimulate repair of fractures and non-unions. Other less well-known outcomes attributed to bio-electrical stimulation are positive bone density changes (Tabrah, 1990), and prevention of osteoporosis (Chang, 2003). A recent report offered adjunctive evidence that stimulation with pulsed electromagnetic field (PEMF) significantly accelerates bone formed during distraction osteogenesis (Fredericks, 2003).

A disadvantage of most electrotherapeutic devices now available, however, is that they often rely on direct implantation of electrodes (or entire electronic packages), or they rely on inductive coupling through the skin using coils which generate time-varying magnetic fields, thereby inducing weak eddy currents within body tissues which inefficiently provide the signal to tissues. Consequently, in addition to bulky coils these systems require relatively large signal generators and battery packs. The need for surgery and biocompatible materials in the one case, and excessive circuit complexity and input power in the other, has kept the price of most such apparatus relatively high, and has also restricted the application of such devices to highly trained personnel. Further, it is noted that TENS (Class II) medical devices are contra-indicated for use on the head.

Accordingly, there remains a need for a versatile, cost-effective system that can be used to provide bioelectric stimulation in a wide range of applications, including healing acceleration and pain relief. There is also a need in the art for a bioelectric stimulation system that is power efficient, capable of being powered by safe, low-voltage batteries, and can reduce the likelihood of a shock hazard.

The present disclosure is directed to overcoming one or more of the shortcomings set forth above, and/or providing further related advantages.

BRIEF SUMMARY

In one aspect, the present disclosure is directed to an apparatus to provide a non-transcranial electrical stimulus to a biological subject. The term "non-transcranial electrical stimulation" generally refers to the non-evasive induction, delivery, and/or generation of an electrical current without substantially inducing, delivering, and/or generating, an electrical current across a region of the brain. Conversely, the term "transcranial electrical stimulation" or "cerebral electrical stimulation" generally refers to the non-evasive induction, delivery, and/or generation, of an electrical current across a region of the brain. Transcranial electrical stimulation has been used to, for example, directly stimulate the brain with low-level direct current, or to activate the motor cortex thorough the skull.

In some embodiments, the apparatus includes a support structure, at least one waveform generator, and at least a first electrode and a second electrode. The support structure can be sized and dimensioned to be worn on a head of the biological subject.

The at least one waveform generator can be carried by the support structure and configured to generate an electrical waveform. In some embodiments, the at least one waveform generator is configured to generate one or more waveforms selected from continuous waveforms, pulse waveforms, single-sine waveforms, multi-sine waveforms, frequency-swept sine waveforms, step waveforms, square waveforms, triangular waveforms, saw-tooth waveforms, arbitrary waveforms, generated waveforms, chirp waveforms, non-sinusoidal waveforms, ramp waveforms, regular or irregular waveforms, or combinations thereof, including single and multi-frequency formed waves.

The at least first and second electrodes are carried by the support structure and are electrically coupled to the waveform generator. The improvement includes the spacing of the first and second electrodes such that the first electrode is sufficiently spaced apart from the second electrode so as to generate a first non-transcranial therapeutic electric stimulus operable to flow through a region within the biological subject in response to a generated electrical waveform from the at least one waveform generator.

In some embodiments, at least one of the first electrode or second electrode may include a first electrically conductive contacting surface. The first electrically conductive contacting surface is adapted to contact a surface of the biological subject and to provide the first non-transcranial therapeutic electric stimulus to the biological subject.

In another aspect, the present disclosure is directed to a method for providing a non-transcranial electrical stimulus to a biological subject. The method employs a wearable electrotherapy system adapted to be worn on a head of the biological subject, the wearable electrotherapy system is configured to retain at least a first plurality of electrodes proximate to at least one temporomandibular joint of the biological subject, when the wearable electrotherapy system is worn. The improvement includes spacing the first plurality of electrodes sufficiently spaced apart so as to generate an electric field within the biological subject in response to a first electric current, without generating an appreciable electric field across a region of the brain of the biological subject.

In some embodiments, the method may further include applying a sufficient amount of an electrical current to the first plurality of electrodes so as to generate a non-transcranial electric field in a region that encompasses at least one temporomandibular joint of the biological subject.

In yet another aspect, the present disclosure is directed to a method for treating a condition associated with a temporomandibular joint disorder. The improvement includes delivering a first non-transcranial electric current from a first electrode assembly located proximate to a first temporomandibular joint of a biological subject. The method may further include delivering a second non-transcranial electric current from a second electrode assembly located proximate to a second temporomandibular joint of the biological subject.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements, as drawn, are not intended to convey any information regarding the actual shape of the particular elements, and have been solely selected for ease of recognition in the drawings.

FIG. 8 is a schematic view of an effective electrical stimulus waveform in pulse mode for promoting proliferation of bone cells, according to one illustrated embodiment.

FIG. 9 is a schematic view of an effective electrical stimulus waveform in continuous mode for promoting proliferation of bone cells, according to one illustrated embodiment.

DETAILED DESCRIPTION

In the following description, certain specific details are included to provide a thorough understanding of various disclosed embodiments. One skilled in the relevant art, however, will recognize that embodiments may be practiced without one or more of these specific details, or with other methods, components, materials, etc. In other instances, well-known structures associated with electrically powered devices including but not limited to voltage and/or current regulators have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment," or "an embodiment," or "in another embodiment," or "in some embodiments," means that a particular referent feature, structure, or characteristic described in connection with the embodiment is included in at least one embodiment. Thus, the appearance of the phrases "in one embodiment," or "in an embodiment," or "in another embodiment," or "in some embodiments," in various places throughout this specification are not necessarily all referring to the same embodiment. Furthermore, the particular features, structures, or characteristics may be combined in any suitable manner in one or more embodiments.

It should be noted that, as used in this specification and the appended claims, the singular forms "a," "an," and "the" include plural referents unless the content clearly dictates otherwise. Thus, for example, reference to an apparatus to provide a non-transcranial electrical stimulus to a biological subject including a "support structure" includes a single support structure, or two or more support structures. It should also be noted that the term "or" is generally employed in its sense including "and/or" unless the content clearly dictates otherwise.

Figure 1:
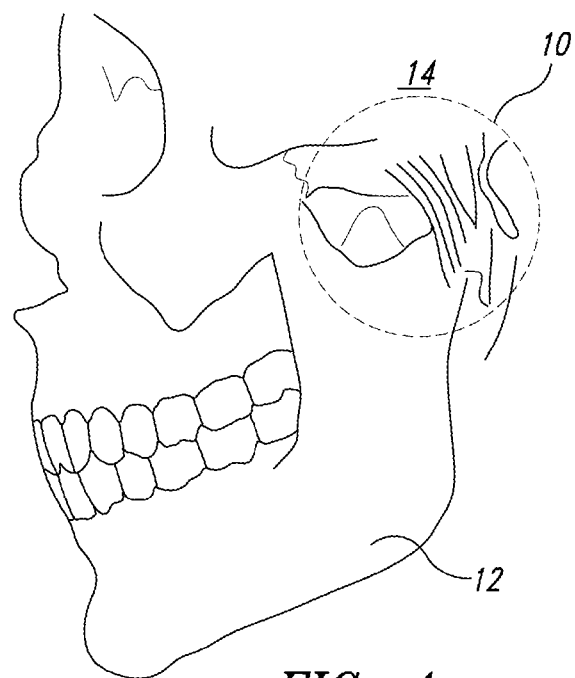
FIG. 1 is a side view of a mandible, temporal bone, and temporomandibular joint of biological subject according to one illustrated embodiment.
Figure 2:
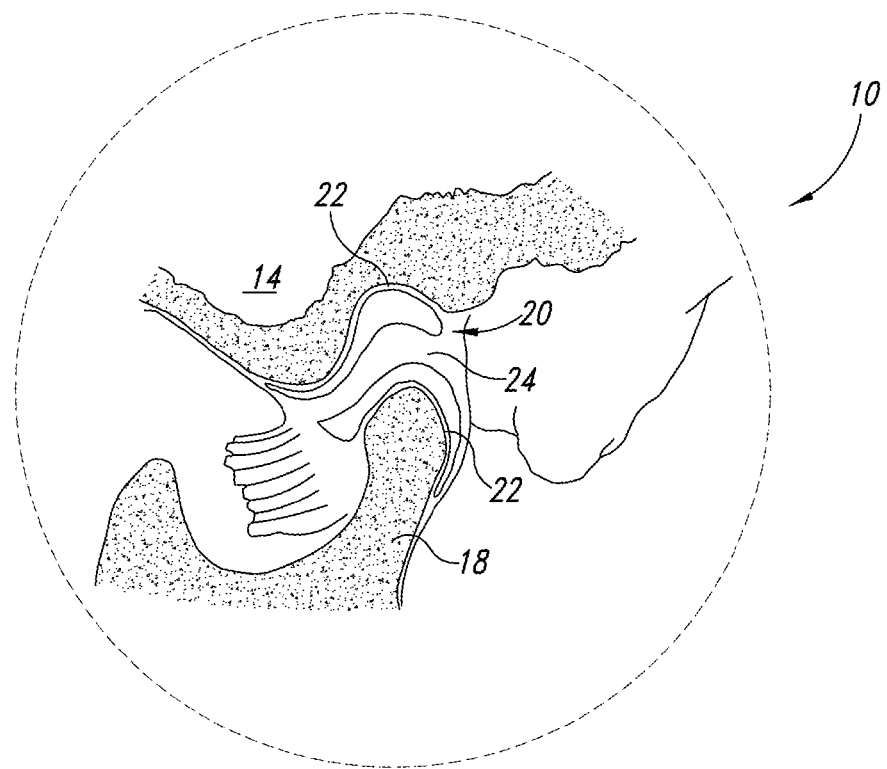
FIG. 2 is an exploded cross-sectional view of a portion of the temporomandibular joint of FIG. 1 according to one illustrated embodiment.

As shown in FIGS. 1 and 2, the temporomandibular joint 10 is the ball-and-socket joint located on each side of the head where the lower jawbone (mandible) 12 joins the temporal bone 14 of the skull. The normal human skull has two temporomandibular joints, one on the right and one on the left.

The lower jawbone 12 has rounded ends (condyles) 18 that glide in and out of the joint socket 20 during talking, chewing, or yawning. As show in FIG. 2, the surfaces of the condyle 18 and the socket of the temporal bone 14 are covered with cartilage 22 and separated by a small articular disk 24 (also known as the meniscus), which absorbs shock and keeps the movement smooth. The articular disk 24 divides the joint cavity into two small spaces and provides the gliding surface for the condyle 18, resulting in smooth joint movement. Muscles enable opening and closing of the mouth, and stabilize the temporomandibular joint 10.

As previously noted, the term temporomandibular joint disorder encompasses a whole spectrum of conditions and diseases associated with pain and/or dysfunction in the jaw joint and the muscles that control jaw movement. In some embodiments, the problem of reliving pain or stimulating healing of a condition associated with temporomandibular joint disorder is solved by applying an electric stimulus (e.g., low energy waveforms (such as those provided by MedRelief®), transcutaneous electrical nerve stimulation (TENS), interferential current therapy (IFC) stimulus, and the like, or combinations thereof) to a region including a temporomandibular joint 10. In some embodiments, the problem of relieving pain or stimulating healing of a condition associated with temporomandibular joint disorder is solved by the delivery of a bioelectrical stimulus optimized to correspond to natural body signals resulting in accelerated and more permanent healing. In some embodiments, one or more of the disclosed electrical stimuli described herein uniquely conforms to natural signals and consequently tissues subjected to electrostimulation undergo less physiological stress when compared to electrostimulation from previous devices.

Figure 3:
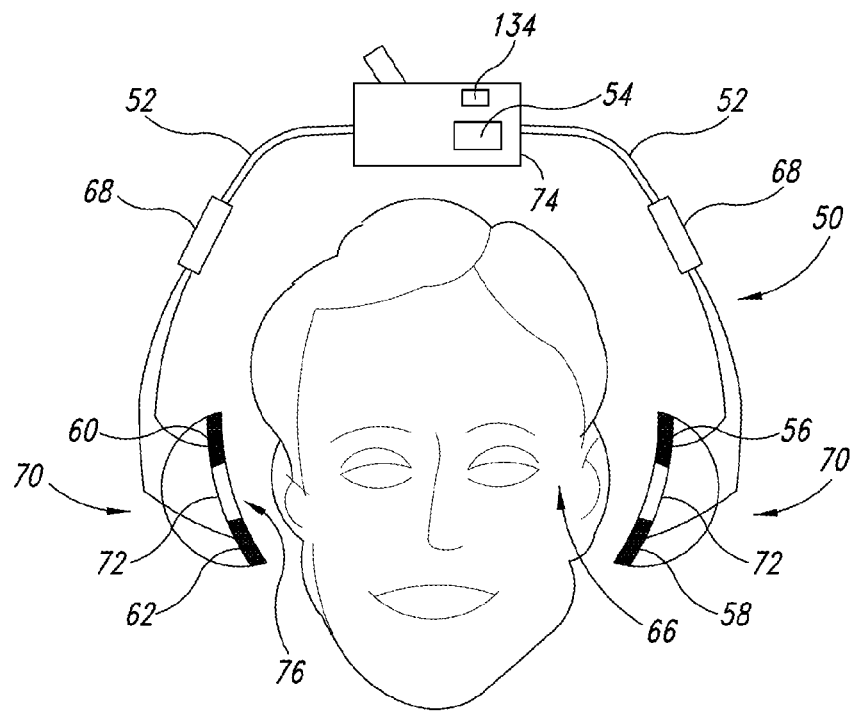
FIG. 3 is a front view of user wearing an apparatus, in the form of a wearable electrotherapy system adapted to be worn on a head of a user, for providing a non-transcranial electrical stimulus to the user, according to one illustrated embodiment.

FIG. 3 shows an exemplary apparatus 50 for providing a non-transcranial electrical stimulus to a biological subject. The apparatus 50 includes a support structure 52, at least one waveform generator 54, and at least a first electrode 56 and a second electrode 58. In some embodiments, the apparatus 50 may further include at least a third electrode 60 and a fourth electrode 62.

The support structure 52 can be sized and dimensioned to be worn on a head of a user. Any suitable structure may be used as the support structure 52. Examples of the support structure 52 include headsets, headbands, fastening clips (sized and dimensioned to be worn on or over an ear), earbuds, ear-cups, and the like. In some embodiments, the support structure 52 is constructed and arranged to transfer a portion of a force applied by the support structure 52 to a temporal region 66 of the user so as to maintain the first and second electrodes 56, 58 relatively stationary with respect to a region proximate an ear and/or a temporomandibular joint 10 of a user. The support structure 52 can include a fastening clip configured to surround an ear of the biological subject and maintain the first and second electrodes 56, 58 proximate an ear and/or a temporomandibular joint 10 of a user. In some embodiments, the support structure 52 is constructed and arranged to quickly and conveniently affix one or more of the electrodes around an ear and/or proximate the temporomandibular joint 10 of a user. The support structure 52 may include one or more fitting assemblies 68 for adjusting the position of the one or more electrodes carried by the support structure 52. In some embodiments, the fitting assemblies 68 permit symmetrically or asymmetrically adjustment of the length of the support structure 52.

In some embodiments, the apparatus 50 may include one or more over-the-ear structures 70, such as, for examples headphones, earphones, noise cancelling headphones, earcups, sound-attenuating earcups, sound-blocking cups, cup-shaped shells, and the like coupled to the support structure 52. The over-the-ear structures 70 may further include, for example, a component that covers a portion or the entire ear, or a component that simply surrounds an ear of the user. In some embodiments, one or more of the electrodes may be incorporate or connected to the over-the-ear structures 70. In some embodiments, part or most of the skin contacting surfaces of the over-the-ear structures 70 may be electrically conductive and serve as electrodes. In some embodiments, some or all of the electrodes, stimulation circuitry, and power is contained within the over-the-ear structures 70.

In some embodiments, the apparatus 50 may include one or more earphone units 72, with each earphone unit 72 having a transducer 76 operable to output an audio signal. In some embodiments, the apparatus 50 may include an ambient noise cancelling apparatus 74 coupled to a noise cancelling-circuit 77. In some embodiments, the ambient noise cancelling apparatus 74 is operable to provide a noise cancelling signal to the transducer 76 to provide active acoustic noise cancellation when the apparatus 50 is worn by the biological subject.

In some embodiments, electrically isolated left and right channels are provided. Alternatively, a wireless audio feature might be provided with, for example, an FM tuner built in and powered by the same battery as the stimulator. An inexpensive FM modulator could then act as bridge between the headphones and a non-broadcast source.

In some other embodiments, the first and the second electrodes 56, 58 are sufficiently spaced apart so as to generate a localized electric field in tissue associated with a temporomandibular joint 10 of the biological subject such that at least 10% of the localized electric field passes through the temporomandibular joint 10. In some embodiments, the first and the second electrodes 56, 58 are spaced apart by the presence of a suitable electrically insulation material.

In some other embodiments, the first electrode 56 is spatially positioned in the range from about twice the length of a temporomandibular joint 10 to about four times the length of temporomandibular joint 10 away from the second electrode 58. In some embodiments, the apparatus 50 may further comprise a third electrode 60 and a fourth electrode 62 carried by the support structure and electrically coupled to the waveform generator, the third electrode 60 being sufficiently spaced apart from the fourth electrode 62 so as to generate a second non-transcranial therapeutic electric stimulus operable to flow through a region within the biological subject in response to a generated electrical waveform from the at least one waveform generator 54.

In some embodiments, the apparatus 50 includes a first coupling member between the support structure and the first and the second electrodes 56, 58, and a second coupling member between the support structure 52 and the third and the fourth electrodes 60, 62, the first and second coupling members configured to releasably hold the first and the second electrodes 56, 58, and the third and the fourth electrodes 60, 62, respectively. In some embodiments, the apparatus 50 is operable to allow operation of the first, the second, the third, and the fourth electrodes 56, 58, 60, 62 individually or jointly. In some embodiments, the apparatus 50 is operable to allow concurrent or sequential operation of the first and the second electrodes 56, 58, and the third and a fourth electrodes 60, 62.

The at least one waveform generator 54 is carried by the support structure 52 and configured to generate an electrical waveform. In some embodiments, the waveform generator 54 may comprise at least one of a processor, a wave-shaping circuit, a digital signal processor based waveform generator, and the like. The waveform generator 54 may be coupled (for example, electrically, wirelessly, and/or inductively coupled or connected) to a one or more of the electrodes and operable to generated an electrical waveform when activated.

In some embodiments, the least one waveform generator 54 is configured to generate one or more waveforms selected from single-sine waveforms, multi-sine waveforms, frequency-swept sine waveforms, step waveforms, pulse waveforms, square waveforms, triangular waveforms, saw-tooth waveforms, arbitrary waveforms, generated waveforms, chirp waveforms, non-sinusoidal waveforms, ramp waveforms, or combinations thereof, including single and multi-frequency formed waves. In some embodiments, the least one waveform generator 54 is operable to generate low energy waveforms such as those provided by MedRelief®), transcutaneous electrical nerve stimulation (TENS), interferential current therapy (IFC) stimulus, and the like, or combinations thereof.

In some embodiments, the generated waveform comprises intermittent bursts of quasi-rectangular waves (waves of generally rectangular shape but typically somewhat distorted), based on a plurality of relatively long primary timing intervals T1, T2 and so forth, forming in succession a primary repeating cycle; a plurality of shorter secondary timing intervals t1, t2 and so forth, into which at least one of said primary intervals is divided, and forming in succession a secondary repeating cycle which continues throughout the length of that primary interval, while at least one other of said primary intervals is not so divided; and a plurality of constant voltage or current levels L1, L2 and so forth, one of which is selected during each primary timing interval or, if that interval is divided, during each secondary timing interval within it. The series of constant current or voltage levels which are selected during successive timing intervals comprises the waveform. The average magnitude of these levels selected during a given primary interval determines the signal amplitude within that interval, and the signal amplitudes within all primary intervals, taken in succession, comprise the envelope of the waveform.

In some embodiments, the waveforms generated by the waveform generator 54 can be used to provide electrical stimuli and waveforms that enable specific actions on biological tissues. Osteochondral tissues are shown herein to respond differently to markedly different frequencies and waveforms.

In some embodiments, the waveforms generated by the waveform generator 54 comprises alternating rectangular or quasirectangular pulses having opposite polarities and unequal lengths, thereby forming rectangular, asymmetric pulse trains. Pulses of specific lengths have been theorized to activate specific cell biochemical mechanisms, especially the binding of calcium or other small, mobile, charged species to receptors on the cell membrane, or their (usually slower) unbinding. The portions of such a train having opposite polarities may balance to yield substantially a net zero charge, and the train may be either continuous or divided into pulse bursts separated by intervals of substantially zero signal. Stimuli administered in pulse-burst mode have similar actions to those administered as continuous trains, but their actions may differ in detail due to the ability (theoretically) of charged species to unbind from receptors during the zero-signal periods, and required administration schedules may also differ.

In some embodiments, a PEMF (pulsed electromagnetic field) is administered via electromagnetic coils. In some embodiments a PEF (pulsed electric field) is administered via electrochemical means (i.e., skin-attached capacitively coupled electrodes). Both PEMF and PEF may employ a repetition of pulse train, and/or individual pulses. In some embodiments, the burst width (duration of the signal) may vary; however, the underlying signal itself remains the same for both PEMF and PEF. In certain alternative embodiments, the pulse train may contain an added signal for no net charge.

Figure 5:
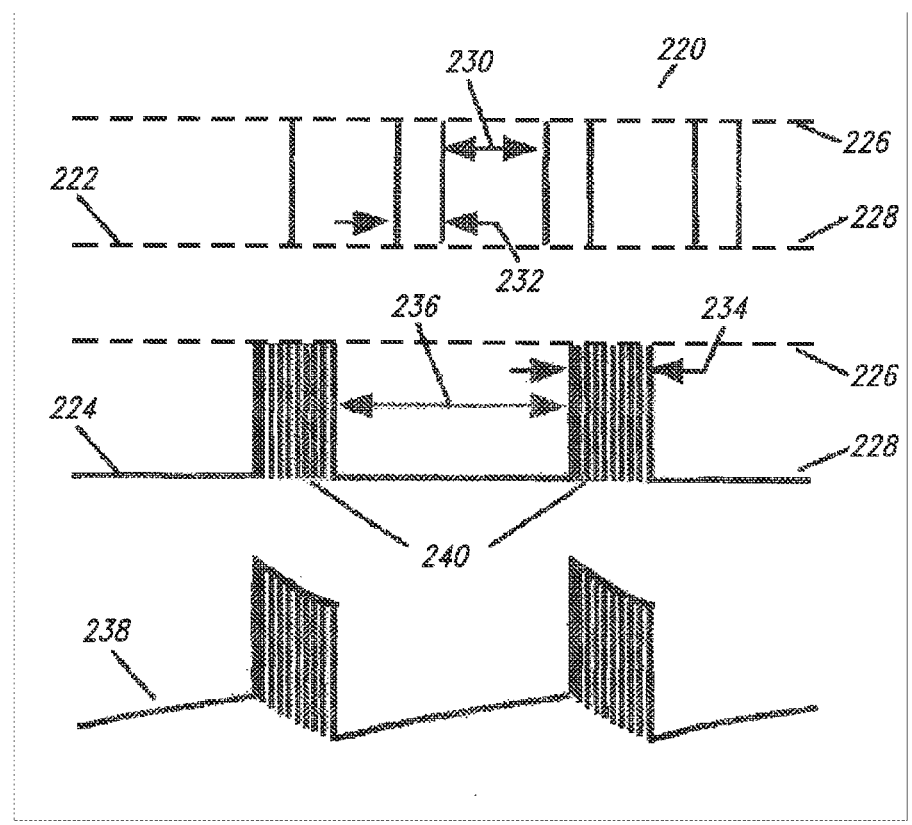
FIG. 5 is a schematic view of a waveform used in stimulating bone fracture healing according to one illustrated embodiment.

FIG. 5 shows a schematic view of a base waveform 220 effective for stimulating bone and cartilage tissue, where a line 222 represents the waveform in continuous mode, and a line 224 represents the same waveform on a longer time scale in pulse-burst mode, levels 226 and 228 represent two different characteristic values of voltage or current, and intervals 230, 232, 234, and 236 represent the timing between specific transitions. Levels 226 and 228 are usually selected so that, when averaged over a full cycle of the waveform, there is no net direct-current (DC) component although levels 226 and 228 may be selected to result in a net positive or net negative DC component if desired. In real-world applications, waveform such as 220 is typically modified in that all voltages or currents decay exponentially toward some intermediate level between levels 226 and 228, with a decay time constant preferably longer than interval 234. The result is represented by a line 238. The waveforms described herein generally have two signal components: a longer component shown as interval 230 and a shorter component shown as interval 232 relative to each other.

Variation in the short and long signal component lengths confers specific effects of a stimulated tissue. In some embodiments, the pulse lengths of interest may be defined as follows, in order of increasing length. Length $\alpha$: between 5 and 75 μsec in duration, in some embodiments between 10 and 50 μsec in duration, in some embodiments between 20 and 35 μsec in duration, and in some embodiments between about 28 μsec in duration. Length $\beta$: between 20 and 100 μsec in duration, preferably between 40 and 80 μsec in duration, in some embodiments between 50 and 70 μsec in duration, and in some embodiments about 60 μsec in duration. Length $\gamma$: between 100 and 1000 μsec in duration, in some embodiments between 150 and 800 μsec in duration, in some embodiments between 180 and 500 μsec in duration, and in some embodiments about 200 μsec in duration. Length $\delta$: in excess of 1 millisecond in duration, in some embodiments between 5 and 100 msec in duration, in some embodiments between 10 and 20 msec in duration, and in some embodiments about 13 msec in duration.

Figure 6:
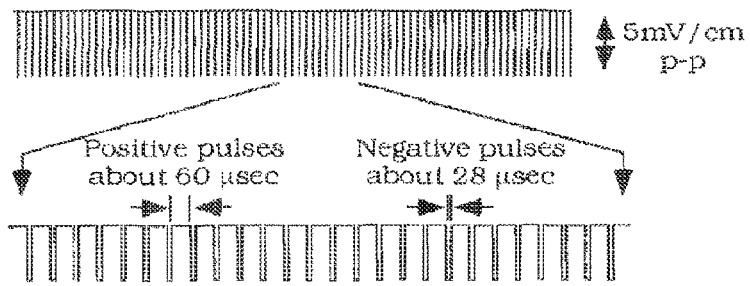
FIG. 6 is a schematic view of an effective electrical signal waveform in pulse mode based on an inductive coil waveform, which is adapted for skin application for promoting mineralization of bone, according to one illustrated embodiment.

In some embodiments, the electrical signal has a shorter component of length α and a longer component of length β: thus having, with the most preferable pulse lengths of each type (28 μsec and 60 μsec respectively), a frequency of about 11.4 KHz. Signals comprised of pulses alternately of length α and length β are referred to herein as "type A" signals and their waveforms as "type A" waveforms. An example a "type-A signal administered as a continuous pulse train is shown in FIG. 6. These signals may be useful for promoting the proliferation of a tissue sample or culture for a variety of biological or therapeutic applications.

Figure 7:
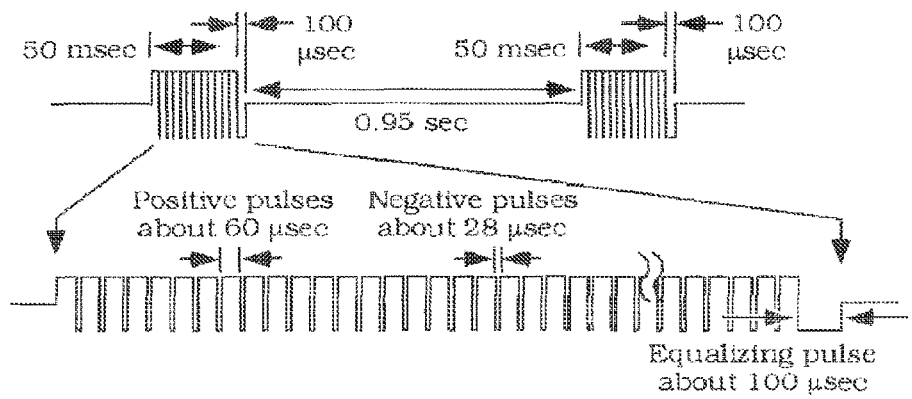
FIG. 7 provides an illustration showing an effective electrical stimulus waveform in continuous mode for promoting mineralization of bone, according to one illustrated embodiment.

In pulse-burst mode, "type A" waveforms would be turned on in bursts 240 of about 0.5 to 500 msec, in some embodiments about 50 msec, with bursts 240 repeated at 0.1-10 Hz or preferably about 1 Hz. An example of this type of waveform is shown in FIG. 7.

In some embodiments, the electrical signal has a shorter component of length α but a longer component of length γ: thus having, in some embodiments, pulse lengths of each type (28 μsec and 200 μsec respectively), a frequency of about 4.4 KHz. Signals comprised of pulses alternately of length α and length γ are referred to herein as "type B" signals and their waveforms as "type B" waveforms. Such waveforms were previously described in U.S. patent application Ser. No. 10/875,801 (publication No. 2004/0267333). An example of a "type-B" signal administered as a continuous pulse train is shown in FIG. 8. These signals are useful in pain relief and in promoting bone healing, and also stimulate the development of cancellous-bone-like structures in osteoblast cultures in vitro, with applications to the field of surgical bone repair and grafting materials.

In pulse-burst mode, "type B" waveforms are turned on in bursts of about 1 to 50 msec, in some embodiments about 5 msec, with bursts repeated at 5-100 Hz or in some embodiments about 15 Hz. An example of this type of waveform is shown in FIG. 9. This waveform is similar in shape and amplitude to effective currents delivered by typical inductive (coil) electromagnetic devices that are commonly used in non-union bone stimulation products e.g. EBI MEDICA, INC® (Parsippany, N.J.) and ORTHOFIX, INC® (McKinney, Tex.).

In some embodiments, the electrical signal has a shorter component of length β but a longer component of length γ: thus having, with the most preferable pulse lengths of each type (60 μsec and 200 μsec respectively) a frequency of about 3.8 KHz. Signals comprised of pulses alternately of length β and length γ are referred to herein as "type C" signals and their waveforms as "type C" waveforms. These signals are useful in promoting bone regeneration, maturation, and calcification.

In pulse-burst mode, "type C" waveforms are turned on in bursts of about 1 to 50 msec, in some embodiments about 5 msec, with bursts repeated at 5-100 Hz or in some embodiments about 15 Hz, much the same as "type B." This waveform is similar in shape and amplitude to effective currents delivered by other typical inductive (coil) electromagnetic devices commonly used in non-union bone stimulation products, e.g. the ORTHOFIX, INC® (McKinney, Tex.) PhysioStim Lite®, which is designed to promote healing of spinal fusions.

In some embodiments, the electrical signal has a shorter component of length γ and a longer component of length δ: thus having, in some embodiments, pulse lengths of each type (200 μsec and 13 msec respectively) a frequency of about 75 Hz. Signals comprised of pulses alternately of length γ and length δ are referred to herein as "type D" signals and their waveforms as "type D" waveforms. These signals are useful especially in promoting cartilage healing and bone calcification, and in treating or reversing osteoporosis and osteoarthritis. While broadly similar to that delivered through electrodes by the BIONICARE MEDICAL TECHNOLOGIES INC® BIO-1000™, as shown in FIG. 3 of U.S. Pat. No. 5,273,033, the "type D" signal differs substantially in wave shape (it is rectangular rather than exponential) and in the fact that it is preferably charge-balanced.

In pulse-burst mode, "type D" waveforms are turned on in bursts of at least 100 msec, in some embodiments about 1 second, with bursts repeated at intervals of one second or more.

The signal intensity may also vary; indeed, more powerful signals often give no more benefit than weaker ones, and sometimes less. For a typical signal (such as the signal of FIG. 5), a peak effectiveness typically falls somewhere between one and ten microamperes per square centimeter ($\mu A/cm^2$), and a crossover point at about a hundred times this value. Beyond this point, the signal may slow healing or may itself cause further injury.

Of particular relevance to the present methods are electrical signals or waveforms that run in continuous mode instead of burst mode. (For example FIG. 6 or 8). Continuously run signals have effects similar to those of pulse-burst signals, but may require different delivery regimes to achieve similar results.

In some embodiments, the applied average current densities of the disclosed waveforms range from about 0.1 to about 1000 microamperes per square centimeter. In some embodiments, the applied average current densities range from about 0.3 to about 300 microamperes per square centimeter. In some embodiments, the applied average current densities range from about 1 and 100 microamperes per square centimeter, and in some embodiments about 10 microamperes per square centimeter, resulting in voltage gradients ranging between 0.01 and 1000, 0.03 and 300, 0.1 and 100, and 1 and 10 microamperes per centimeter, respectively, in typical body tissues. The individual nearly-square wave signal is asynchronous with a long positive segment and a short negative segment or vice versa. The positive and negative portions balance to yield a zero net charge or optionally may be charge imbalanced with an equalizing pulse at the end of the pulse to provide zero net charge balance over the waveform as a whole. These waveforms delivered by skin electrodes use continuous rectangular or approximately rectangular rather than sinusoidal or strongly exponentially decaying waveforms. Other waveforms useful in conjunction of the disclosed methods are disclosed in, for example, published U.S. patent application Ser. No. 10/875,801 (publication No. 2004/0267333).

In some embodiment, one or more of the disclosed electrical stimuli may be administered to cells, biological tissues, or individuals in need of treatment for intermittent treatment intervals or continuously throughout the day. A treatment interval is defined herein as a time interval that a waveform is administered in pulse or continuous mode. Treatment intervals may be about 10 minutes to about 4 hours in duration. In some embodiments, the treatment intervals may be from about 30 minutes to about 2.5 hours in duration. In some embodiments, the treatment intervals are about 1 hour in duration. Treatment intervals may occur between about 1 and 100 times per day. The duration and frequency of treatment intervals may be adjusted for each case to obtain an effective amount of electrical stimulation to promote cell proliferation, cell differentiation, bone growth, development, pain relief, repair, or the like. The parameters are adjusted to determine the most effective treatment parameters.

Signals do not necessarily require long hours of duration in the treatment interval although 24 hour administration may be used if desired. Typically, 30 minutes (repeated several times a day) is required for biological effectiveness. In vitro cell proliferation may be measured by standard means such as cell counts, increases in nucleic acid or protein synthesis. Upregulation or down regulation of matrix proteins (collagen types I, III, and IV) as well as growth factors and cytokines (such as TGF-B, VEGF, SLPI, FN, MMPs) may also be measured (mRNA and protein synthesis). In vivo effects may be determined by rate of healing of an injury or measuring bone mass density. Other diagnostic methods for proliferation, differentiation, or mineralization of bone tissue may be employed.

In one embodiment, proliferation-promoting and differentiation-promoting signals are used sequentially. This combination of waveforms is used to increase the cell number and then promote differentiation of the cells. As an example, the sequential use of proliferation and differentiation signals may be used to promote proliferation of osteoblasts and then differentiation of the osteoblasts into mineral producing osteocytes that promote mineralization of bone or vice versa. For example, a treatment paradigm may be used where a proliferation-promoting A-type signal is administered first to a cell population in vitro or ex vivo for hours, days or weeks and then the proliferation promoting signal is replaced with a mineralization-promoting B-type signal for hours, days or weeks until bone mineralization has been effected. The tissue produced may then be transplanted for patient benefit. Both signals may also be applied simultaneously to promote both proliferation, and differentiation and mineralization simultaneously.

The electric signals may be delivered by skin electrodes, or electrochemical connection. Skin electrodes are available commercially in sizes such as 1½×12, 2×3½, and 2×2 inches. These reusable electrodes are advantageous because they do not contain latex and have not shown significant skin irritation. The reusable electrodes can be used multiple times; also reducing costs to the patient. Such electrodes may include those by Koalaty Products Inc (Tampa, Fla.) or by Vermed, Inc. (Bellows Falls, Vt.).

There are multiple advantages of using skin electrodes instead of electromagnetic coils. Firstly, skin electrodes are more efficient. With electrodes, only the signal which will actually be sent into the body must be generated. With a coil, because of poor electromagnetic coupling with the tissues, the signal put in must be many, many times stronger than that desired in the tissues. This makes the required generating circuitry for electrodes potentially much simpler than for coils, while requiring much less power to operate. Secondly, skin electrodes are more user friendly. Skin electrodes have at most a few percent of the weight and bulk of coils needed to deliver equivalent signal levels. Similarly, because of better coupling efficiency the signal generators to drive electrodes can be made much smaller and lighter than those for coils. After a short time, a wearer hardly notices they are there. Thirdly, skin electrodes are more economical. Unlike coils, which cost hundreds to thousands of dollars each, electrodes are "throw-away" items typically costing less than a dollar. Also, because of greater efficiency and simplicity, the signal generators and batteries to drive them can be small and inexpensive to manufacture compared with those for coils. Fourthly, skin electrodes permit simpler battery construction and longer battery life facilitating the ease and patient compliance of using the device. Lastly, skin electrodes are more versatile than electromagnetic coils. Coils must be built to match the geometric characteristics of body parts to which they will be applied, and each must be large enough to surround or enclose the part to be treated. With electrodes, on the other hand, current distribution is determined by electrode placement only and readily predictable throughout the volume between.

In some embodiments, the waveforms generated by the waveform generator 54 can be useful in methods to promote the growth and repair of bone tissue in vivo. For example, stimulation with A-type waveforms (FIGS. 6 and 7) promotes proliferation of cells. A-type waveforms may also result in an increase in bone morphogenic proteins to promote differentiation. In some embodiments, an increase in BMP-2 and BMP-7 production is effected using A-type or to a lesser degree, B-type electrical signals. This effect is highly valuable and provides a method for enhancing the generation of sufficient tissue for proper tissue healing in vivo, or to creating tissue grafts. This signal is also valuable for providing sufficient cell mass for infiltration into a polymer scaffold for tissue engineering purposes. In another embodiment, as demonstrated by in vitro testing, stimulation in vivo provides proliferation and differentiation of osteoblasts to increase the number of osteoblasts for mineralization. Such an increase in number of cells provides a method for filling in gaps or holes in developing or regenerating bone through electrical stimulation. Cells generated through proliferation induced by A-type waveforms may be used immediately, or preserved using conventional cell preservation methods until a future need arises.

Stimulation with B-type waveforms (FIGS. 8 and 9) promotes proliferation to a small degree, and has actions different than A-type waveforms.

Actions promoted by B-type waveforms include, but are not limited to mineralization, extracellular protein production, and matrix organization. The actions of B-type waveforms are also valuable and provide methods to enhance the mineralization step and ossification of new bone tissue. In one embodiment, developing or regenerating bone tissue is stimulated with B-type waveforms to enhance the rate of mineralization. It has been proposed that B-type waveforms may act through calcium/calmodulin pathways and also by stimulation of G-protein coupled receptors or mechanoreceptors on bone cells. (Bowler, Front Biosci, 1998, 3:d769-780; Baribault et al., Mol Cell Biol, 2006, 26(2):709-717). As such, methods are also provided to modulate the activity of calcium/calmodulin-mediated actions as well as G protein coupled receptors and mechanoreceptors using electrical stimulation. Modulation of these cellular pathways and receptors are valuable to promote the growth and repair of bone tissue in vitro or in vivo.

Stimulation with C-type waveforms promotes bone regeneration, maturation, and calcification. These waveforms are also valuable and provide methods to enhance the mineralization step and ossification of new bone tissue.

Stimulation using D-type waveforms promotes cartilage development and healing and bone calcification, and is useful for treating or reversing osteoporosis and osteoarthritis. Applications of these waveforms include in vivo applications such as repairing damaged cartilage, increasing bone density in patients with osteoporosis.

Methods are also provided for combination or sequential use of the waveforms described herein for the development of a treatment regime to effect specific biological results on developing or regenerating osteochondral tissue.

In some embodiments, fractures in patients with a bone disorder may be treated with signals to heal fractures and then strengthen the bone. As a non-limiting example of this embodiment, an osteoporotic patient with a fracture may be treated by first stimulating with an A-type signal to promote proliferation and release of growth factors and then a B-type waveform to promote an increase in bone density at the site of repair to increase bone mass density and prevent refracture.

In another embodiment, combining two or more types of waveforms described herein may be used to promote the sequential proliferation, differentiation, and mineralization of osteochondral tissues. As a non-limiting example of this embodiment, a culture of osteoblasts may be grown under the influence of a A-type signal in connection with or prior to connection with a polymeric matrix. After seeding the polymeric matrix, B-type signals are then administered to the cell-matrix construct to promote mineralization of a construct useful as a bone graft.

In another embodiment, two or more signals may be administered simultaneously to promote concomitant proliferation, differentiation, and mineralization of osteochondral tissue in vivo or in vitro. Different signals may also be applied sequentially to osteochondral tissue in order to yield a greater effect than delivering either signal alone. The sequential process may be repeated as needed to produce additional tissue (such as bone) by cycling through the two-step process enough times to obtain the desired biological effect. As a specific non-limiting example, A-type signals may be applied first to produce more bone cells by proliferation and then B-type signals may be applied to induce the larger number of bone cells to produce more bone tissue (matrix, mineral and organization) and then repeated if needed. The amount of bone produced using repetition of a sequential stimulation protocol would be greater than that produced by either signal alone or in combination.

In some embodiments, the least first electrode 56 and a second electrode 58 are carried by the support structure 54 and coupled (for example, electrically, wirelessly, and/or inductively coupled or connected) to the waveform generator 54, the first electrode 56 being sufficiently spaced apart from the second electrode 58 so as to generate a first non-transcranial therapeutic electric stimulus operable to flow through a region within the biological subject in response to a generated electrical waveform from the at least one waveform generator 54, at least one of the first electrode 56 or the second electrode 58 having a first electrically conductive contacting surface 70. In some embodiments, the first electrically conductive contacting surface 70 is adapted to contact a surface of the biological subject and to provide the first non-transcranial therapeutic electric stimulus to the biological subject. In some other embodiments, the first electrically conductive contacting surface conforms to a biological surface proximate to a temporomandibular joint 10 of the biological subject. For example, in some embodiments, the first electrically conductive contacting surface is adapted to conform to the outer contours of a biological surface such as an ear, a skin region proximate and/or overlying a temporomandibular joint 10, and the like. In some embodiments, the first electrically conductive contacting surface is adapted to lie over and/or press against one or more acupuncture points found on a biological surface (e.g., an outer surface of an ear, regions proximate a temporomandibular joint, and the like).

In some other embodiments, at least part of the first electrode 56, the second electrode 58, or both comprises at least one electrically conductive material selected from, silver plated textiles, textiles interwoven with conductive materials, textiles interwoven with silver threads, semiconductor materials, graphite fibers, carbon nanotubes, conductive plastics, conductive polymers, and the like.

Figure 4:
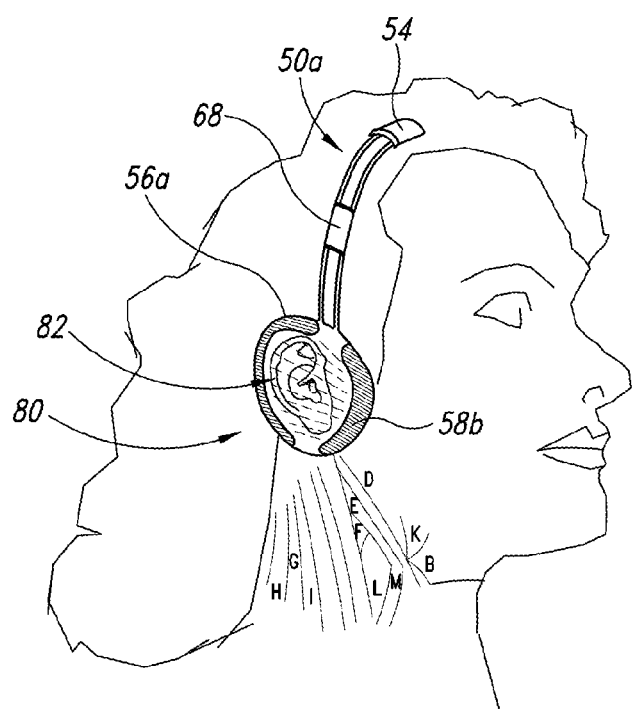
FIG. 4 is a side view of user wearing an apparatus, in the form of a headset including electrodes configured to surround an ear, for providing a non-transcranial electrical stimulus to the user according to another illustrated embodiment.

Referring to FIGS. 3 and 4, in some embodiments, the apparatus 50 takes the form of a wearable electrotherapy system 50a adapted to be worn on a head of the biological subject and to provide non-transcranial therapeutic electric stimulus. The wearable electrotherapy system 50a is configured to retain at least a first plurality of electrodes 80 proximate to at least one temporomandibular joint 10 of the biological subject when the wearable electrotherapy system 50a is worn. In some embodiments, the first plurality of electrodes 80 is sufficiently spaced apart so as to generate an electric field 82 within the biological subject in response to a first electric current. In some embodiments, the wearable electrotherapy system 50a includes electrodes 56a, 58b configured to surround an ear, for providing a non-transcranial electrical stimulus to the user according to another illustrated embodiment. In some embodiments, the wearable electrotherapy system 50a provides the user convenient walk around freedom while receiving non-transcranial therapeutic electric stimuli.

Figure 10:
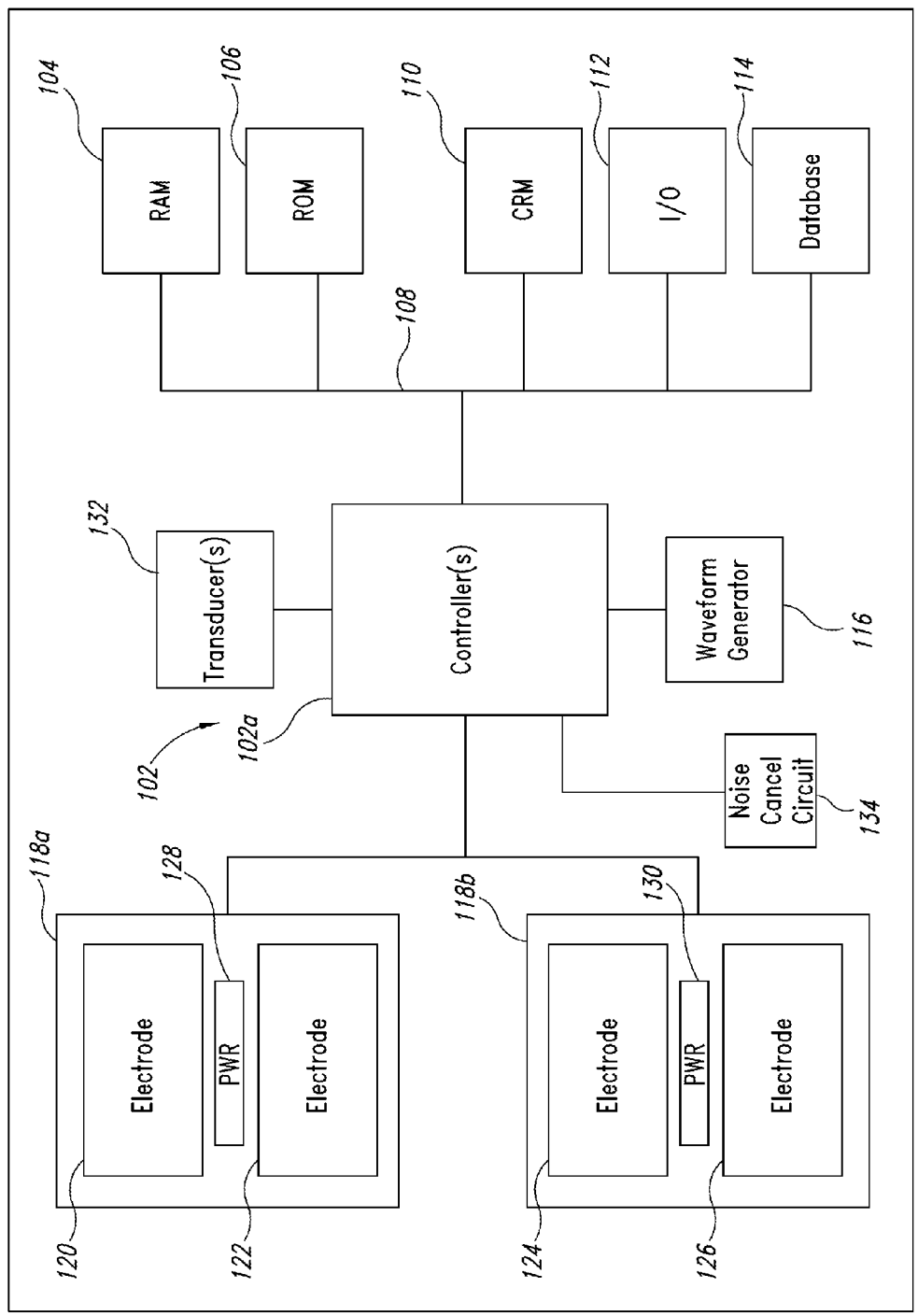
FIG. 10 is a schematic diagram of a system for providing a non-transcranial electrical stimulus to a biological subject, according to one illustrated embodiment.
Figure 11:
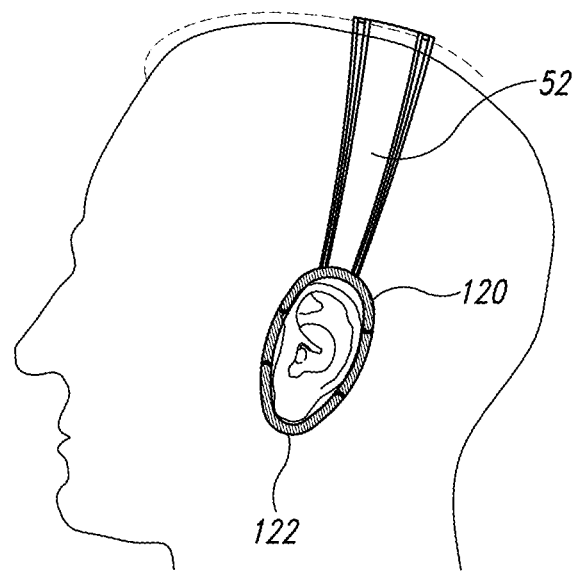
FIG. 11 is a side view of a user wearing an apparatus, in the form of a headset including electrodes configured to surround an ear, for providing a non-transcranial electrical stimulus to the user, according to another illustrated embodiment.
Figure 12:
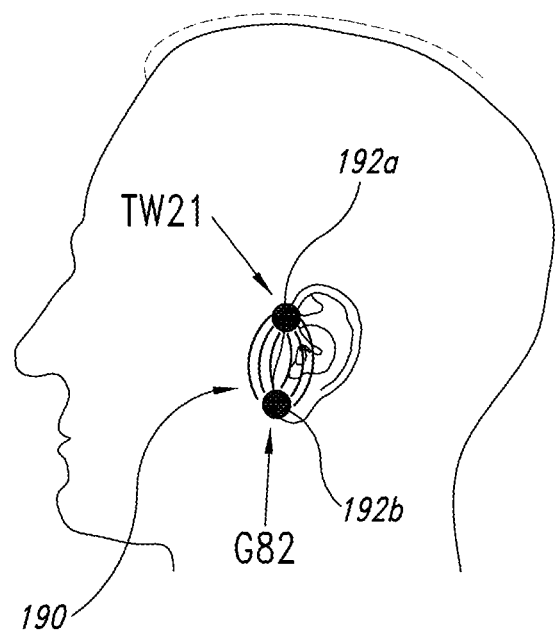
FIG. 12 is side view of an electric field distribution in a region encompassing a temporomandibular joint of the biological subject, according to one illustrated embodiment.

FIG. 10 shows a block diagram of a system 100 suitable to provide, for example, a non-transcranial electrical stimulus to a biological subject. The system 100 may include one or more controllers 102 such as a microprocessor 102a, a central processing unit (CPU), a digital signal processor (DSP), an application-specific integrated circuit (ASIC), a field programmable gate array, or the like, or combinations thereof, and may include discrete digital and/or analog circuit elements or electronics.

The system 100 may further include one or more memories that store instructions and/or data, for example, random access memory (RAM) 104, read-only memory (ROM) 106, or the like, coupled to the controller 102 by one or more instruction, data, and/or power buses 108. The system 100 may further include a computer-readable media drive or memory slot 110, and one or more input/output components 112 such as, for example, a graphical user interface, a display, a keyboard, a keypad, a trackball, a joystick, a touch-screen, a mouse, a switch, a dial, or the like, or any other peripheral device. The system 100 may further include one or more databases 114. The system 100 may further include at least one waveform generator 116, and a first plurality of electrodes 118a including at least a first electrode 120 and a second electrode 122. In some embodiments, the system 50 may further include a second plurality of electrodes 118b including at least a third 124 and a fourth electrode 126. In some other embodiments, the system 100 may further include at least one power source 128, 130 electrically coupleable to at least one of the first 120 and the second electrodes 122.

In some embodiments, the problem of providing an electrical stimulus to a region associated with a temporomandibular joint 10 of a biological subject without providing an appreciable electrical stimulus to a brain of a biological subject is solved by providing a wearable electrotherapy system 100 adapted to be worn on a head of the biological subject. The wearable electrotherapy system 100 is configured to retain at least a first plurality of electrodes 118a proximate to at least one temporomandibular joint 10 of the biological subject when the wearable electrotherapy system 100 is worn, and is operable to deliver a non-transcranial electrical stimulus.

In some embodiments, the waveform generator 116 comprises at least one of a processor, a wave-shaping circuit, a digital signal processor based waveform generator, and the like, or combinations thereof. In some embodiments, the controller 102 is electrically coupled to the at least one waveform generator 116 and operable to control the waveform generator 116. In some embodiments, a processor is electrically coupled to the at least one waveform generator 116 and operable to control the waveform generator 116.

The computer-readable media drive or memory slot 110 may be configured to accept computer-readable memory media. In some embodiments, a program for causing the system 100 to execute any of the disclosed methods can be stored on a computer-readable recording medium. Examples of computer-readable memory media include CD-R, CD-ROM, DVD, data signal embodied in a carrier wave, flash memory (e.g., SD cards, compact flash cards, USB flash drives, memory sticks, multimedia cards, or the like), floppy disk, hard drive, magnetic tape, magnetooptic disk, MINI-DISC, non-volatile memory card, EEPROM, optical disk, optical storage, RAM, ROM, system memory, web server, or the like.

In some embodiments, the system 100 is configured to deliver a non-transcranial electrical current that passes through tissue associated with a temporomandibular joint 10 of the biological subject in response to a generated electrical waveform from the at least one waveform generator 116 when in use.

In some embodiments, the first electrode 120 is sufficiently spaced apart from the second electrode 122 so as to induce a non-transcranial electrical current that passes through tissue associated with a temporomandibular joint 10 of the biological subject in response to a generated electrical waveform from the at least one waveform generator 116. In some other embodiments, the first electrode 120 is sufficiently spaced apart from the second electrode 122 so as to generate a non-transcranial electrical current to a region of the biological subject such that a major portion of the generated non-transcranial electrical current is spaced apart from the brain of the biological subject and passes through tissue associated a temporomandibular joint 10. In some other embodiments, the first and the second electrodes 120, 122 are spatially separated so as to deliver a pulsed electrical current to a region of the biological subject including a temporomandibular joint 10, when activated.

In some embodiments, the system 100 may further include one or more transducer 132 operable to output an audio signal. In some embodiments, the system 100 may further include an ambient noise cancelling component coupled to a noise cancelling-circuit 134. In some embodiments, the ambient noise cancelling component is operable to provide a noise cancelling signal to the transducer to provide active acoustic noise cancellation when the system 100 is worn by the biological subject.

Referring to FIGS. 11 through 15, in some embodiments, the first and the second electrodes 120, 122 are sufficiently spaced apart so as to generate a substantially prolate spheroidical electric field 190 encompassing a temporomandibular joint 10 of the biological subject in response to a generated electrical waveform from the at least one waveform generator 116. In some other embodiments, the first and the second electrodes 120, 122 are positioned with respect to one another so as to generate a non-transcranial electrical field 190 occupying a substantially prolate spheroidical region proximate to an ear of the biological subject, when the first and the second electrodes 120, 122 are activated. In some other embodiments, the first and the second electrodes 120, 122 are sufficiently spaced apart so as to transdermally deliver a non-transcranial electrical current to a temporomandibular joint 10 of the biological subject, when a potential is applied to the first and the second electrodes 120, 122.

In some embodiments, the non-transcranial electrical field 190 generated between the first electrode 120 and the second electrode, includes the temporomandibular joint 10 while having its endpoints located on Acupuncture points TW21 192a and G82 192b (collectively 192).

Figure 13:
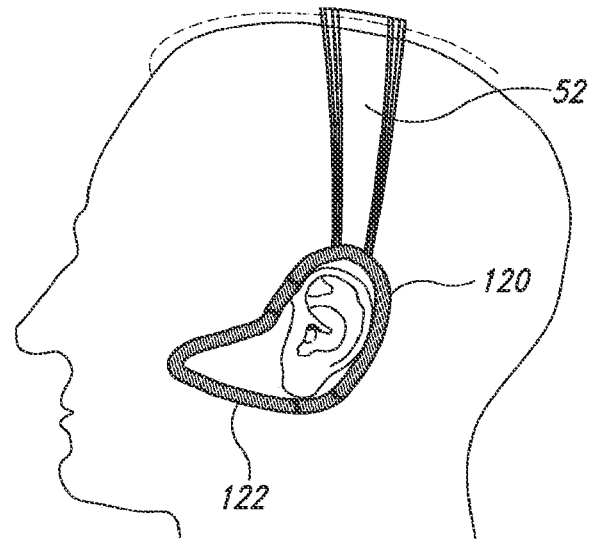
FIG. 13 is a side view of a user wearing an apparatus, in the form of a headset including electrodes configured to surround an ear, for providing a non-transcranial electrical stimulus to the user, according to another illustrated embodiment.
Figure 14:
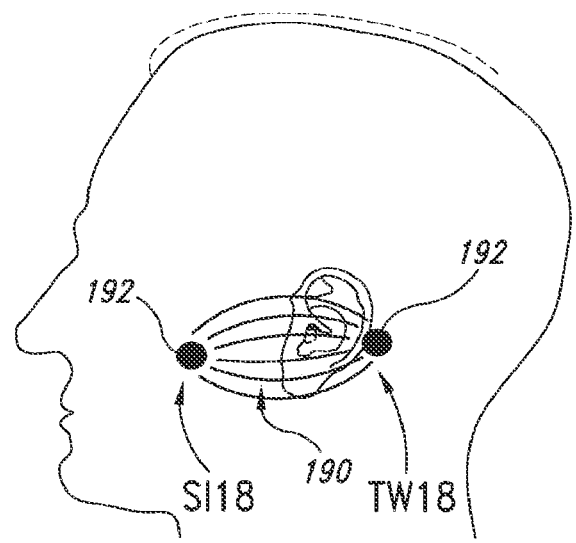
FIG. 14 is side view of an electric field distribution in a region encompassing a temporomandibular joint of a biological subject, according to another illustrated embodiment.
Figure 15:
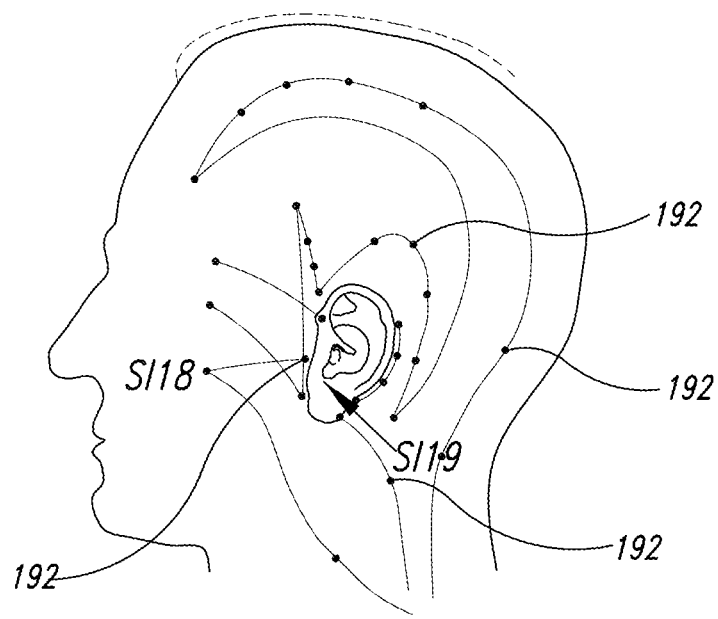
FIG. 15 is a side view depiction of acupuncture points associated with the left side of the head of a biological subject, according to one illustrated embodiment.

Referring to FIG. 15, in some embodiments, one or more over-the-ear structures 70 can be configured to lie over, press against, and/or electrically stimulate one or more acupuncture points found on or proximate the ear and/or the temporomandibular joint 10 of the biological subject. For example, the apparatus 50 can include one or more over-the-ear structures 70 (FIG. 3) that are operable to electrically stimulate auricular acupuncture points of a user to relive a condition associated with a temporomandibular joint 10 disorder. For example, as shown in FIG. 13, in some embodiments, electrode 122 can be placed in contact with a region immediately in front of the ear and electrode while electrode 120 can be made to conform to the rear curve of the ear and contact a region immediately behind the ear, such the each electrode 120, 122 encompasses one or more acupuncture points 192a, 192b (e.g., acupuncture points associated with the Gall bladder (G82), Triple Warmer points (TW 18, 19, 20 and 21), the small intestine points (SI 18, and 19,), and the like). According, when activated, the spaced apart electrodes 120, 122 would generate an electric field 190 encompassing a temporomandibular joint 10, and one or more acupuncture points 192.

Figure 16:
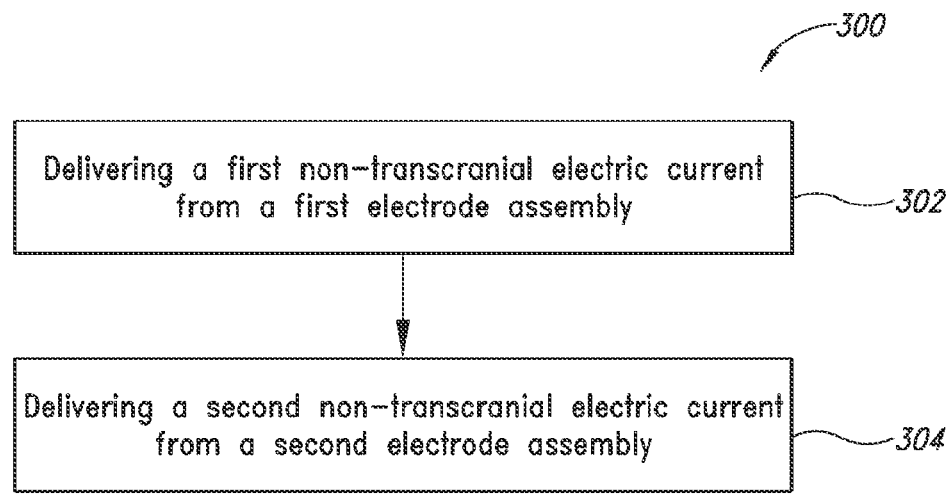
FIG. 16 is a flow diagram of a method for treating a condition associated with a temporomandibular joint disorder, according to one illustrated embodiment.

FIG. 16 shows an exemplary method 300 for treating a condition associated with a temporomandibular joint disorder.

At 302, the method 300 includes delivering a first non-transcranial electric current from a first electrode assembly located proximate to a first temporomandibular joint of a biological subject.

At 304, the method 300 includes delivering a second non-transcranial electric current from a second electrode assembly located proximate to a second temporomandibular joint of the biological subject.

In some embodiments, delivering the first non-transcranial electric current includes providing a sufficient current to transdermally deliver an electrical current to the first temporomandibular joint of the biological subject, and delivering the sufficient amount of the second non-transcranial electric current includes providing a sufficient current to transdermally deliver an electrical current to the second temporomandibular joint of the biological subject. In some embodiments, delivering the first non-transcranial electric current and delivering the second non-transcranial electric current includes alternating between delivering the first non-transcranial electric current and delivering the second non-transcranial electric current for a selected time period.

In some embodiments, delivering the first non-transcranial electric current includes supplying a sufficient amount of current to generate a non-transcranial electrical current field encompassing the first temporomandibular joint, and delivering the second non-transcranial electric current includes supplying a sufficient amount of current to generate a non-transcranial electrical current encompassing the second temporomandibular joint. In some embodiments, delivering the first non-transcranial electric current, and delivering the second non-transcranial electric current includes delivery of the first non-transcranial electric current for a first time period, followed by delivery of the second non-transcranial electric current for a second time period.

Figure 17:
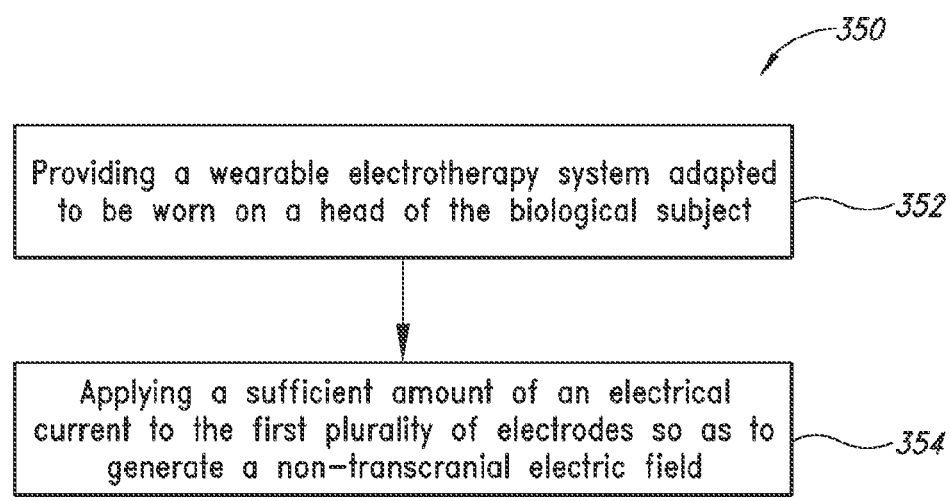
FIG. 17 is a flow diagram of a method for providing a non-transcranial electrical stimulus to a biological subject, according to one illustrated embodiment.

FIG. 17 shows an exemplary method 350 for method for providing a non-transcranial electrical stimulus to a biological subject.

At 352, the method 350 includes providing a wearable electrotherapy system adapted to be worn on a head of the biological subject. In some embodiments, the wearable electrotherapy system is configured to retain at least a first plurality of electrodes 118a (FIG. 10) proximate to at least one temporomandibular joint 10 of the biological subject when the wearable electrotherapy system is worn, the first plurality of electrodes 118a (FIG. 10) being sufficiently spaced apart so as to generate an electric field within the biological subject in response to a first electric current.

At 354, the method 350 includes applying a sufficient amount of an electrical current to the first plurality of electrodes 118a (FIG. 10) so as to generate a non-transcranial electric field in a region that encompasses at least one temporomandibular joint 10 (FIGS. 1 and 2) of the biological subject.

In some embodiments, applying the sufficient amount of the electrical current to the first plurality of electrodes 118a (FIG. 10) comprises transdermally delivering an electrical current to the at least one temporomandibular joint 10 (FIGS. 1 and 2) of the biological subject. In some embodiments, applying the sufficient amount of the electrical current to the first plurality of electrodes 118a (FIG. 10) comprises generating a substantially prolate spheroidical electric field encompassing the at least one temporomandibular joint 10 (FIGS. 1 and 2) of the biological subject.

In some embodiments, applying the sufficient amount of the electrical current to the first plurality of electrodes 118a (FIG. 10) comprises providing an electrical current flow that occupies a region proximate to an ear of the biological subject. In some embodiments, applying the sufficient amount of the electrical current to the first plurality of electrodes comprises providing a sufficient amount of current to generate a non-transcranial electrical current encompassing the temporomandibular joint 10 (FIGS. 1 and 2), wherein a major portion of the non-transcranial electrical current is space apart from the brain of the biological subject.

The various embodiments described above can be combined to provide further embodiments. All of the U.S. patents, U.S. patent application publications, U.S. patent applications, foreign patents, foreign patent applications, and non-patent publications referred to in this specification and/or listed in the Application Data Sheet, including but not limited to:

U.S. Pat. No. 5,273,033 issued on Dec. 28, 1993; U.S. Pat. No. 6,011,994 issued Jan. 4, 2000; U.S. Pat. No. 6,321,119 issued Nov. 20, 2001; U.S. Pat. No. 6,535,767 issued Mar. 18, 2003; U.S. Pat. No. 7,117,034 issued Oct. 3, 2006; U.S. Patent Pub. No. 2004/0267333 published Dec. 30, 2004; U.S. Patent Pub. No. 2006/0293724 published Dec. 28, 2006; and U.S. Patent Pub. No. 2008/0039901 published Feb. 14, 2008; are each incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for treating a condition associated with a temporomandibular joint disorder, the method comprising:
capacitively delivering a first non-transcranial electric current from a first electrode assembly of a first electrode and a second electrode to at least partially flow through a first temporomandibular joint on a sagittal first side of a head of a biological subject, the first electrode positioned on a point proximate and externally anterior of a first ear of the biological subject on the first sagittal first side of the head and the second electrode positioned on a point on the sagittal first side of the head spaced apart from the first electrode.

2. The method of claim 1 wherein capacitively delivering the first non-transcranial electric current includes providing a sufficient current to transdermally capacitively deliver an electrical current to the first temporomandibular joint of the biological subject.

3. The method of claim 1 wherein capacitively delivering the first non-transcranial electric current includes supplying a sufficient amount of current to capacitively generate a non-transcranial electrical current field encompassing the first temporomandibular joint.

4. The method of claim 1, further comprising:
capacitively delivering a second non-transcranial electric current from a second electrode assembly of a third electrode and a fourth electrode to at least partially flow through a second temporomandibular joint on a sagittal second side of the head of the biological subject, the third electrode located positioned on a point proximate and externally anterior of a second ear of the biological subject on the sagittal second side of the head and the fourth electrode positioned on a point on the sagittal second side of the head spaced apart from the third electrode.

5. The method of claim 4 wherein capacitively delivering the first non-transcranial electric current and capacitively delivering the second non-transcranial electric current includes alternating between capacitively delivering the first non-transcranial electric current and capacitively delivering the second non-transcranial electric current for a selected time period.

6. The method of claim 4 wherein capacitively delivering the first non-transcranial electric current, and capacitively delivering the second non-transcranial electric current includes capacitive delivery of the first non-transcranial electric current for a first time period, followed by capacitive delivery of the second non-transcranial electric current for a second time period.

7. The method of claim 4 wherein capacitively delivering the second non-transcranial electric current includes providing a sufficient current to capacitively transdermally deliver an electrical current to the second temporomandibular joint of the biological subject.

8. The method of claim 4 wherein capacitively delivering the second non-transcranial electric current includes capacitively supplying a sufficient amount of current to generate a non-transcranial electrical current encompassing the second temporomandibular joint.

9. A method for providing a non-transcranial electrical stimulus to a biological subject using a wearable electrotherapy system adapted to be worn on a head of the biological subject, the wearable electrotherapy system configured to retain at least a first pair of electrodes externally anterior to a first ear and disposed across a first temporomandibular joint of the biological subject when the wearable electrotherapy system is worn, the first pair of electrodes being sufficiently spaced apart across the first temporomandibular joint so as to generate an electric field within the biological subject in response to a first electric current, the method comprising:
applying a sufficient amount of an electrical current to the first pair of electrodes so as to capacitively generate a non-transcranial electric field in a region that encompasses at least the first temporomandibular joint of the biological subject.

10. The method of claim 9 wherein applying the sufficient amount of the electrical current to the first pair of electrodes comprises transdermally capacitively delivering an electrical current to the first temporomandibular joint of the biological subject.

11. The method of claim 9 wherein applying the sufficient amount of the electrical current to the first plurality of electrodes comprises generating a substantially prolate spheroidical electric field encompassing the first temporomandibular joint of the biological subject.

12. The method of claim 9 wherein capacitively applying the sufficient amount of the electrical current to the first pair of electrodes comprises capacitively providing an electrical current flow that occupies a region proximate to the first ear of the biological subject.

13. The method of claim 9 wherein capacitively applying the sufficient amount of the electrical current to the first pair of electrodes comprises capacitively providing a sufficient amount of current to generate a non-transcranial electrical current encompassing the first temporomandibular joint, such that a major portion of the non-transcranial electrical current is spaced away from the brain of the biological subject.

* * * * *